US011735031B2

(12) United States Patent
Raziq

(10) Patent No.: US 11,735,031 B2
(45) Date of Patent: Aug. 22, 2023

(54) MEDICAL APPARATUS, METHOD, AND STORAGE MEDIUM TO DETECT IMPACT

(71) Applicant: Canon U.S.A., Inc., Melville, NY (US)

(72) Inventor: Mostafa Raziq, Saugus, MA (US)

(73) Assignee: Canon U.S.A., Inc., Melville, NY (US)

(*) Notice: Subject to any disclaimer, the term of this patent is extended or adjusted under 35 U.S.C. 154(b) by 0 days.

(21) Appl. No.: 17/566,496

(22) Filed: Dec. 30, 2021

(65) Prior Publication Data
US 2023/0215269 A1 Jul. 6, 2023

(51) Int. Cl.
G08B 31/00 (2006.01)
G08B 21/04 (2006.01)
G01P 15/08 (2006.01)
A61B 5/00 (2006.01)
G16H 40/67 (2018.01)
G08B 5/36 (2006.01)

(52) U.S. Cl.
CPC .............. G08B 31/00 (2013.01); A61B 5/721 (2013.01); G01P 15/0891 (2013.01); G08B 5/36 (2013.01); G08B 21/043 (2013.01); G08B 21/0492 (2013.01); G16H 40/67 (2018.01)

(58) Field of Classification Search
CPC ... G01P 15/0891; G01P 15/18; G08B 21/043; A61B 5/721; A61B 5/1117
See application file for complete search history.

(56) References Cited

U.S. PATENT DOCUMENTS

| 5,036,852 A * | 8/1991 | Leishman | G16H 40/67 379/38 |
| 6,827,695 B2 * | 12/2004 | Palazzolo | A61B 5/721 600/509 |
| 7,191,089 B2 | 3/2007 | Clifford et al. | |
| 8,549,892 B2 | 10/2013 | Weber et al. | |
| 9,228,859 B2 * | 1/2016 | Ranky | H10N 30/06 |
| 10,222,396 B2 | 3/2019 | Iv Evangelista et al. | |
| 10,272,010 B2 * | 4/2019 | Freeman | A61N 1/3904 |
| 10,534,014 B2 | 1/2020 | Keal et al. | |
| 10,810,852 B2 * | 10/2020 | Burton | G08B 21/24 |
| 10,827,985 B2 * | 11/2020 | Mayoras, Jr. | A61B 5/742 |
| 11,099,204 B2 * | 8/2021 | Proano | A61B 6/102 |
| 2005/0193829 A1 | 9/2005 | Brinz et al. | |
| 2013/0238048 A1 * | 9/2013 | Almendinger | A61N 1/37276 607/40 |
| 2017/0188946 A1 * | 7/2017 | Klusmann | A61M 1/90 |

* cited by examiner

Primary Examiner — John A Tweel, Jr.
(74) Attorney, Agent, or Firm — Canon U.S.A., Inc. IP Division

(57) ABSTRACT

A medical apparatus, method, or storage medium to perform monitoring a sensor of the medical apparatus to obtain a sensor reading, performing impact detection based on the sensor reading, generating an impact profile based on the impact detection, characterizing the impact detection, and responding to the impact detection.

41 Claims, 5 Drawing Sheets

MEDICAL APPARATUS, METHOD, AND STORAGE MEDIUM TO DETECT IMPACT

BACKGROUND

Field of the Disclosure

The present disclosure generally relates to medical equipment and, more particularly, to a medical apparatus, method, and storage medium to detect impact.

Description of the Related Art

Medical equipment is subject to accidental, inadvertent, unintentional or intentional handling that can cause damage or adversely affect their performance. In hospitals and medical centers, devices can drop, fall, be knocked off a surface, or otherwise can accidentally, intentionally or improperly be mishandled during use or shipment. This can cause equipment malfunction or damage, medical procedure delay, bad imagery, bad device reputation, etc. Medical equipment generally includes diagnostic and therapeutic equipment, surgical instruments, tools, devices, as well as other types of equipment.

Medical equipment is not monitored for impact or damage, does not indicate impact status, does not distinguish between a major or minor impact, does not wirelessly transmit log event files, does not interrogate battery status, is not interrogated remotely, and does not predict field service maintenance.

An MMOCT imaging catheter configuration, for example, can be used for OCT and NIRAF imaging of coronary arteries and for patients who are candidates for transluminal interventional procedures. During MMOCT use at a hospital, medical equipment components such as a PIU assembly are subject to unintentional mishandling, freefall, being knocked off of a surface, etc., thereby causing the PIU assembly to malfunction or be damaged when dropped on the floor. MMOCT configurations do not support PIU assembly impact detection during hospital use, movement, or shipment, do not support a method to notify a user the possibility of the PIU assembly being dropped and damaged, and do not support a catheter/optics/electronics damage detection. MMOCT configurations do not support a visual LED indicator to indicate PIU impact status, do not distinguish between a minor impact or a major impact, do not wirelessly transmit log event files, do not interrogate the PIU remotely, do not interrogate battery status, and do not predict field service maintenance.

U.S. Publication No. 20050193829 discloses detecting damage risk or preventing damage in handheld electronics devices using an integrated motion sensor. To detect damage risk, a shock sensor is positioned in a handheld electronics device, such as on or within a housing of the electronics device. Through a display, communication or other mechanism, shock information is provided to assess a type or amount of damage to a product.

U.S. Pat. No. 8,549,882 discloses a method of measuring drop impact at an electronic device, and includes detecting a fall based on signals from drop detection sensor of the electronic device, receiving an output from a piezoelectric sensor in response to detecting the fall, and storing drop data based on the output from the piezoelectric sensor in a memory at the electronic device.

U.S. Pat. No. 10,222,395 discloses an electronic device for visually representing an impact event. The electronic device includes an accelerometer, a gyroscope, and a magnetometer for measuring its acceleration, angular rotation, and magnetic field intensity relative to its motion. Using any suitable filter, a normalization process is used to standardize readings from the accelerometer, gyroscope, and magnetometer. The electronic device also includes impact location and impact severity determination procedures executable by its processor from its memory module to provide an impact indicator or a visual representation of the impact which may indicate possible damage, shock or fracture incurred on the device. The impact indicator serves as a preview of impacts by displaying gradients of green, yellow and red depicted in increasing severity, i.e., from "no impact" event to "severe impact" event.

A need exists to overcome the drawbacks identified above.

SUMMARY

The present disclosure advantageously monitors or detects a medical apparatus for impact, drop or damage, notifies a user of the medical apparatus being impacted, dropped or damaged, indicates impact status, distinguishes between a major or minor impact, wirelessly transmits log event files, interrogates battery status, enables remote interrogation, and predicts field service maintenance.

According to an aspect of the present disclosure, a medical apparatus, method, or medium can monitor a sensor of the medical apparatus to obtain a sensor reading, perform impact detection based on the sensor reading, generate an impact profile based on the impact detection, characterize the impact detection, and respond to the impact detection.

According to another aspect of the present disclosure, the medical apparatus, method or storage medium can detect damage of the medical apparatus based on the sensor reading, visually indicate impact status of the medical apparatus with one or more LEDs based on the sensor reading, and/or predict field service maintenance of the medical apparatus based on the sensor reading.

According to another aspect of the present disclosure, the sensor reading can be a plurality of sensor readings, and the sensor can include one or more of an acceleration sensor, a gyroscope sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, a depth sensor, and can include other types of sensors.

According to another aspect of the present disclosure, the medical apparatus, method or storage medium can generate an impact log and log the impact profile in the impact log, characterize the impact detection as major, minor, normal, or critical based on one or more sensor readings having a value within or outside of a predetermined range, and/or trigger an event based on the impact detection, and generate a warning based on the impact detection.

According to another aspect of the present disclosure, the medical apparatus, method or storage medium can power the medical apparatus with a power source, interrogate power status of the power source, switch power modes based on activity of the medical apparatus, the power modes including one or more or a combination of a power-on mode, a power-off mode, a sleep mode, and a low power mode.

According to another aspect of the present disclosure, the power source can be a rechargeable battery and the medical apparatus, method and storage medium can charge the battery with a battery charger, interrogate power status of the battery, provide visual indication of the power status of the battery with one or more LEDs, and/or transmit the power status of the battery to one or more computing configurations through a network.

According to another aspect of the present disclosure, the medical apparatus, method or storage medium can provide the medical apparatus with a display with a GUI, wherein the GUI can allow interaction with the medical apparatus through graphics, audio, or combinations thereof.

According to another aspect of the present disclosure, the medical apparatus, method and storage medium can perform wired or wireless communication with the medical apparatus through a network, remotely interrogate the at least one sensor by one or more computing configurations through a network, and can perform sensor reading processing using artificial intelligence or machine learning.

Further features of the present disclosure will become apparent from the following description of exemplary embodiments with reference to the attached drawings, where like structure is indicated with like reference numerals.

DESCRIPTION OF THE EMBODIMENTS

Various exemplary embodiments, features, and aspects of the disclosure that relate to medical apparatuses, methods, and storage mediums to detect impact will be described below with reference to the drawings that may have different characteristics, advantages, disadvantages, performance parameters, or the like.

In the present disclosure, medical apparatus, equipment, device or instrument configurations to detect impact are described that functionally implement intravascular imaging modalities including, for example, multi-modality optical coherence tomography (MMOCT), angiography, OCT, near infrared auto fluorescence (NIRAF), spectrally encoded endoscopy (SEE), ultrasound imaging (US), intravascular ultrasound (IVUS), computed tomography (CT), magnetic resonance imaging (MRI), combinations or hybrids thereof, or the like. The present disclosure is not limited to any particular configuration.

Figure 1:
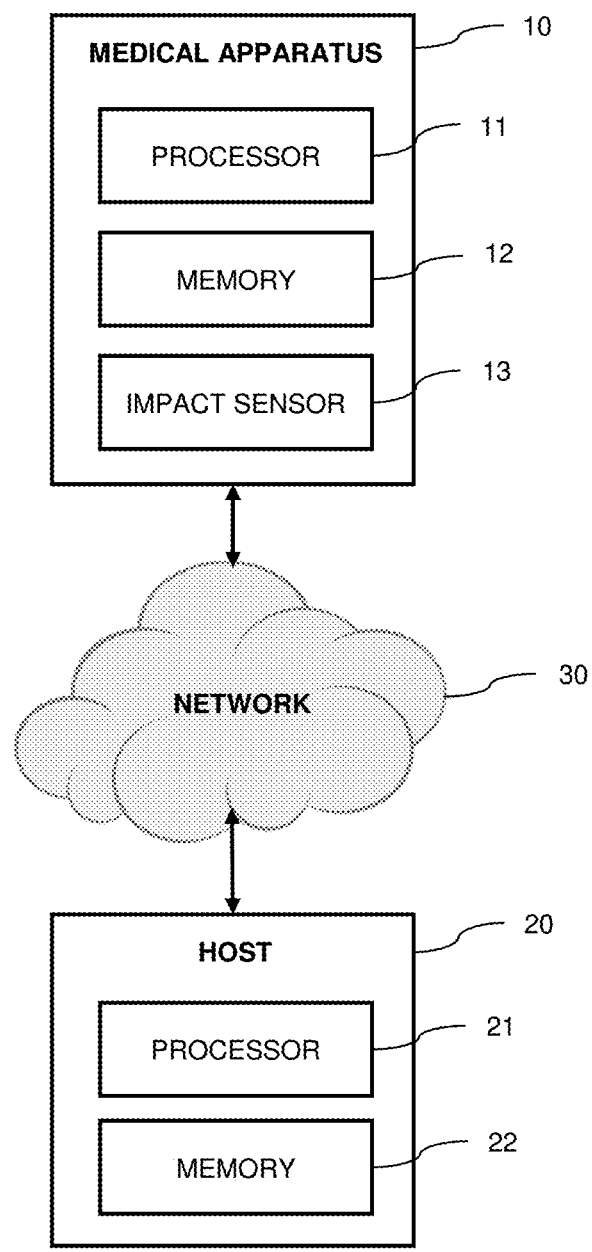
FIG. 1 illustrates an exemplary medical apparatus arrangement or configuration according to one or more embodiments.

FIG. 1 is a diagram illustrating an exemplary medical apparatus 10 according to some embodiments that senses, detects, records, or otherwise monitors impacts, drops, falls, or other conditions of the medical apparatus 10. The medical apparatus 10 can communicatively interconnect to a host 20 through a network 30.

The medical apparatus 10 is subject to accidental, inadvertent, unintentional or intentional handling or movement that can cause damage or adversely affect the performance of the medical apparatus 10. The medical apparatus 10, for example, can impact, drop, fall, be knocked off a surface, or can otherwise be accidentally, intentionally, unintentionally or improperly mishandled or moved during use or shipment. This can cause malfunction, damage, or other adverse results to the medical apparatus 10, such as medical procedure delay, bad imagery, bad device reputation, or the like.

The medical apparatus 10 has one or more or a combination of a processor 11, memory 12, and an impact sensor 13, and can include other components. The processor 11 can be configured as a control circuit or circuitry for performing overall control of the medical apparatus 10, and can execute programs or instructions stored in the memory 12 to perform various data processing or other functions of the medical apparatus 10. The memory 12 can store the instructions, code, programming, software, information, data, or combinations thereof. The sensor 13 can monitor, measure, detect or record various types of data, and the medical apparatus 10 can transmit or send the data to the host 20 through the network 30.

The medical apparatus 10 is configured to monitor or detect for impact, drop, fall, damage, or other events, notify a user of the medical apparatus being impacted, dropped or damaged, indicate impact status, distinguish between a major or minor impact, wirelessly transmit log event files, interrogate battery status, be interrogated remotely, and/or predict field service maintenance.

The medical apparatus 10 supports impact detection during hospital use, movement, or shipment, supports a method to notify a user the possibility of the medical apparatus 10 being dropped and damaged, and supports a catheter/optics/electronics damage detection. The medical apparatus 10 supports visually indicating impact status of the medical apparatus 10 with one or more light emitting diodes (LEDs), supports distinguishing between a minor impact or a major impact, supports wirelessly transmitting log event files, supports remote interrogation of the medical apparatus 10, supports interrogation of battery status, and supports prediction of field service maintenance.

The host 20 has one or more or a combination of a processor 21 and memory 22, and can include other components. The processor 21 can be configured as a control circuit or circuitry for performing overall control of the host 20, and can execute programs or instructions stored in the memory 22 to perform various data processing or other functions of the host 20. The memory 22 can store the instructions, code, programming, software, information, data, or combinations thereof. The host 20 can be configured as one or more or a combination of a server, computer, or other computing configuration. The host 20 can include a transceiver and data can be transferred wirelessly or in a wired manner between the medical apparatus 10 and the host 20 through the network 30. For example, impact readings monitored or recorded by the sensor 13 can be transmitted or sent to the host 20 through the network 30.

The network 30 facilitates wireless or wired transfer of information between the medical apparatus 10 and the host 20. The network 3o can include an internal or external wired or wireless network including one or more or a combination of the Internet, an intranet, a local area network (LAN), a wide areas network (WAN), a public network, a private network, a cellular network, a network interface, an input/output interface, a universal serial bus (USB), wireless fidelity protocol (WiFi), Bluetooth, other network configurations or combinations thereof. The network 30 can include transmission cables, optical transmission fibers, wireless transmission, routers, firewalls, switches gateway computers, servers, or the like. A network adapter card or network interface in each processing device (controller, sensors, storage, or the like) can receive messages and/or instructions from and/or through the network and forward the informational data for storage or execution or the like to the processor 11 or memory 12 of the medical apparatus 10.

The medical apparatus 10 or the host 20 can interrogate the sensor 13 of the medical apparatus 10 to obtain, acquire, process, or log measured or detected characteristics or operational parameters such as sensor readings, impact profiles, impact logs, impact events, log event files, or other types of information based on the measured or detected data of the medical apparatus 10. The sensor readings, impact profiles, log event files, or other measured information can be stored in the memory 12 and/or the memory 22. The sensor readings or detected information can be analyzed or compared with previously stored information associated with the medical apparatus 10. The host 20 can send or transmit the sensor readings or detected or stored information to the medical apparatus 10 through the network 30. The sensor 103 can monitor, measure or detect various types of data of the medical apparatus 10, and can transmit or send the sensor reading data to a host through a network. Maintenance alerts, warnings, or other types of reports can be generated based on the data to extend the life, enhance reliability, warn of damage, or other provide other beneficial or operational characteristics of the medical apparatus 10.

Figure 2:
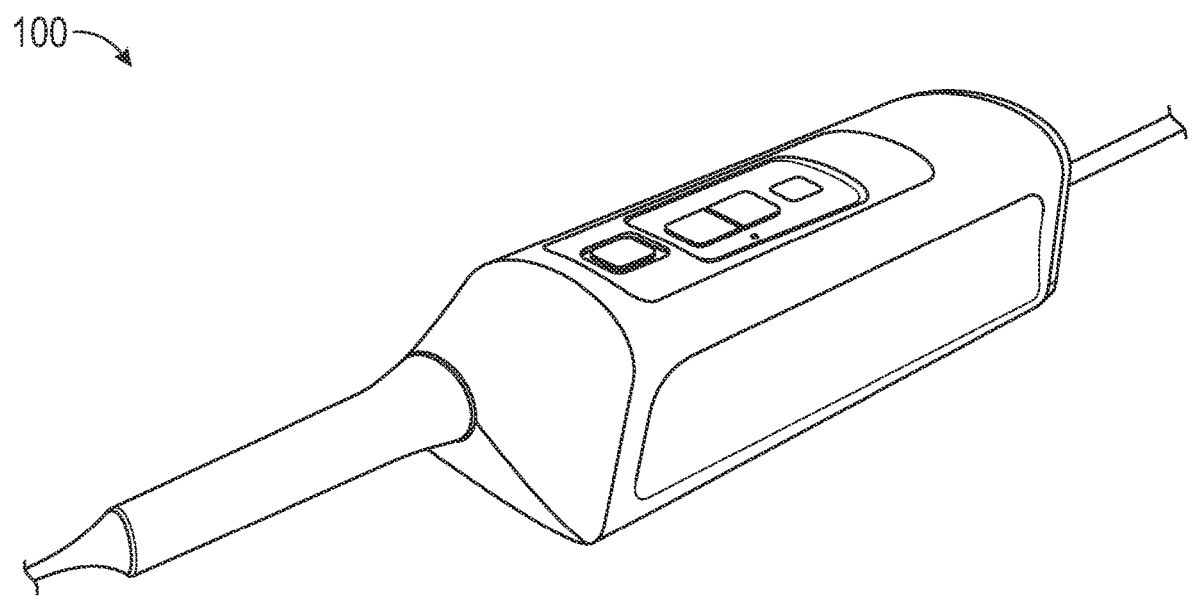
FIG. 2 illustrates a PIU 100 as an exemplary medical apparatus according to one or more embodiments.
Figure 3:
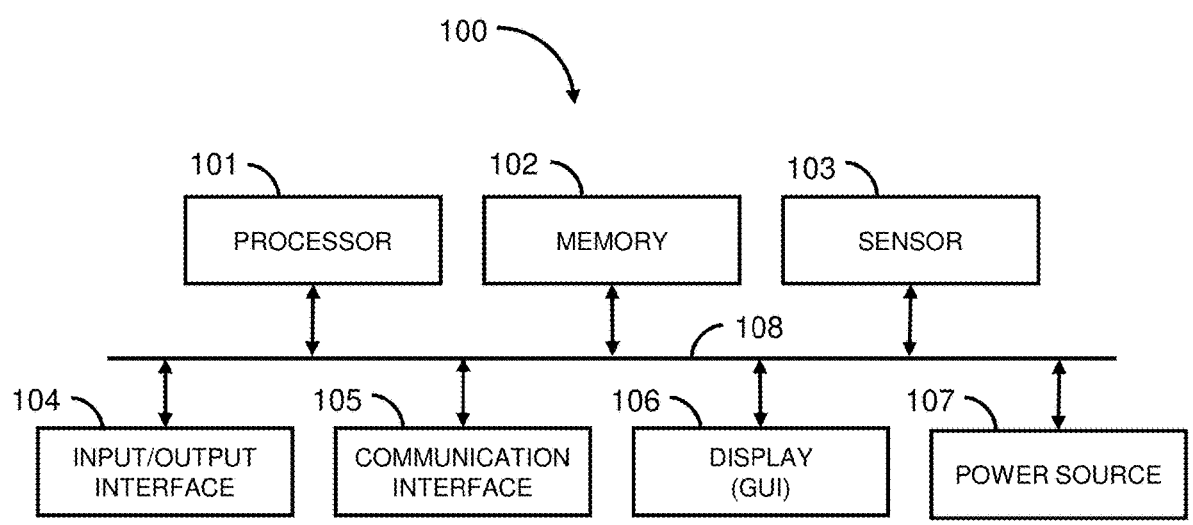
FIG. 3 is a block diagram illustrating an example of a hardware configuration of the PIU 100.

FIG. 2 illustrates a patient interface unit (PIU) 100 as an exemplary medical apparatus according to some embodiments. FIG. 3 is a diagram illustrating an example of a hardware configuration of the PIU 100.

The PIU 100 is configured to measure, detect, sense, record, or otherwise monitor impacts, drops, falls, or other conditions of the PIU 100, and has one or more or a combination of a processor 101, a memory 102, a sensor 103, an input/output interface 104, a communication interface 105, a display 106, and a power source 107, that are operatively interconnected by a bus 108 to perform the functions described herein, and can include other elements or components.

The processor 101 can be configured as a control circuit or circuitry for performing overall control of the PIU 100, and can execute a program, instructions, code or software stored in the memory 102 to perform various data processing, computation, algorithmic tasks, or other functions of the PIU 100. The memory 102 can store the program, information, other data, or combinations thereof. The sensor 103 can monitor, measure or detect various types of data of the PIU 100, and can transmit or send the sensor readings or data to a host through a network. The input/output interface 104 can interconnect various components with the PIU 100 to transfer data or information to or from the PIU 100. The communication interface 105 can interconnect various components with the PIU 100 to facilitate communication to or from or the PIU 100. The display 106 can present a display to a user to view images, data or other information, and can be configured as a liquid crystal display (LCD) or other type of display. The PIU 100 can include one or more keys, buttons, switches, a mouse, a keyboard, or the like, to perform display control of the display 106 and control of input of various kinds of setting or default information set by the input/output interface 104 and the communication interface 105, and to provide inputs to the PIU 100. The power source 107 provides power to the PIU 100 to maintain a regulated power supply to the PIU 100, and can operate in a power-on mode, a power-off mode, and can operate in other modes. The bus 108 communicatively interconnects the components, and connects the PIU 100 to input devices, output devices, communication devices, or other devices. The input devices are configured to enable the user to communicate information and select commands to the PIU 100, and can include one or more or a combination of a mouse, keyboard, touchscreen, or the like, with keys or buttons with alphanumeric, icon, emoji, or other types of symbols. The output devices are configured to display data or images generated by the PIU 100, and can include printers, display devices, or other output configurations.

The processor 101 can be configured as a control circuit or circuitry for performing overall control of the PIU 100, and can be implemented by any combination of hardware, software, and firmware. The processor 101 has one or more or a combination of a controller, microcontroller, microprocessor, integrated circuit, microchip, central processing unit (CPU), graphics processing unit (GPU), digital signal processor (DSP), field-programmable array (FPGA), application specific integrated circuit (ASIC), circuitry, hybrids, and can include other circuitry, elements, or components. The processor 101 can execute programs, instructions, code, software, or combinations thereof, to perform various data processing, computation, logic operations, algorithmic tasks or other functions, where the components, process steps, data structures, or the like can be implemented using one or more operating systems, computing platforms, computer programs, general purpose machines, hardwired devices, that receive input from sensors, detectors, or other devices associated with the PIU 100.

The memory 102 can store various types of data or information used by the PIU 100 including sensor readings, programs, input or output data, or other types of data. The programs can include an operating system (OS) and other types of software. The memory 102 can store instructions and data when the PIU 100 is off or there is no power. The memory 102 can include volatile or non-volatile memory and can be configured as a one or more or a combination of read-only memory (ROM), random access memory (RAM), electrically erasable programmable read-only memory (EEPROM), hard disk drive (HDD), secure digital (SD) card, universal serial bus (USB) flash drive memory, optical disk, floppy disk, mass storage, removable storage, an internal or external storage device, or other types of memory that store a boot program, various kinds of applications, font data, a user file, an edit file, or the like. The ROM stores data and instructions that are implemented by the processor 101 and other instruments or components interconnected with the PIU 100. The RAM functions as a main memory, a work area, or the like of the PIU 100 and is configured to have a memory capacity that is able to be expanded by using an optional RAM connected to an expansion port. The data stored in the memory 102 can be transmitted to a local host or to a network location, such as cloud storage or the like, wirelessly, through a hardwired connection, or combinations thereof. PIU impact log files or other data can also be transferred through an RS232 serial interface. The collected data can be transmitted using any suitable wireless protocol capable of wirelessly transmitting data either in real time or on demand.

The sensor 103 can include one or more or a combination of a processor, detection circuitry, memory, hardware, software, firmware, and can include other circuitry, elements, or components. The sensor 103 can be a plurality of sensors and acquires sensor information output from one or more sensors that detect motion, current position and movement of the PIU 100. The sensor 103 can include a multi-axis acceleration or accelerometer sensor and a multi-axis gyroscope sensor, can be a combination of an acceleration and gyroscope sensors, can include other sensors, and can be configured through the use of a piezoelectric transducer, a mechanical switch, a single axis accelerometer, a multi-axis accelerometer, or other types of configurations. The sensor 103 can monitor, detect, measure, record, or store physical, operational, quantifiable data or other characteristic parameters of the PIU 100 including one or more or a combination of an impact, shock, drop, fall, movement, acceleration, velocity, rotation, temperature, pressure position, orientation, motion, or other types of data of the PIU 100 in multiple axes, in a multi-dimensional manner, along an x axis, a y axis, a z axis, or any combination thereof, and can generate sensor readings, information, data, a digital signal, an electronic signal, or other types of information corresponding to the detected state. The PIU 100 can transmit or send the sensor reading data wirelessly or in a wired manner to a remote host or server. The sensor 103 can be interrogated and can generate a sensor reading signal or information that can be processed in real time, stored, post processed at a later time, or combinations thereof. The information or data that is generated by the sensor 103 can be processed, demodulated, filtered, or conditioned to remove noise or other types of signals. The sensor 103 can include one or more or a combination of an acceleration or accelerometer sensor, a gyroscope sensor, a power sensor, a battery sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, a depth sensor, and can include other types of sensors.

The acceleration sensor, for example, can sense or measure the displacement of mass of the PIU 100 with a position or sense the speed of a motion of the PIU 100. The gyroscope sensor can sense or measure angular velocity or an angle of motion and can measure movement of the PIU 100 in up to six total degrees of freedom in three-dimensional space including three degrees of translation freedom along cartesian x, y, and z coordinates and orientation changes between those axes through rotation along one or more or of a yaw axis, a pitch axis, a roll axis, and a horizontal axis. Yaw is when the PIU 100 twists left or right on a vertical axis. Rotation from side to side is called pitch. Rotation on the front-to-back axis is called roll. The sensor 103 can monitor shock or drop impact with low power consumption, dynamic range, and bandwidth to accurately detect and capture shock events and convert the sensor readings to a digital signal for additional or post processing. An entire shock profile can be characterized by its peak amplitude and pulse width for further analysis. The processor 101 of the PIU 100 can also interrogate the capacity of the power source, and can warn a user to replace the battery at a time when a value of the battery capacity falls below a predetermined threshold amount.

The acceleration sensor can include, for example, a gravity sensor, a drop detection sensor, or the like. The gyroscope sensor can include an angular velocity sensor, a hand-shake correction sensor, a geomagnetism sensor, or the like. The position sensor can be a global positioning system (GPS) sensor that receives data output from a GPS. The longitudinal and latitude of a current position can be obtained from access points of a radio frequency identification device (RFID) and a WiFi device and information output from wireless base stations, for example, so that these detections may be used as position sensors. These sensors can be arranged internally or externally of the PIU 100.

When the PIU 100 moves, an acceleration change and rotation around the gravity axis are detected and the sensor 103 can output the information about the detected change and rotation. The PIU 100 can acquire information about the change and rotation output from the sensor 103 as sensor information. In response to movement of the PIU 100, the sensor 103 can obtain positional information (longitude and latitude, for example) indicative of a place at which the PIU 100 is located (the current position).

The input/output interface 104 is configured to interconnect to one or more or a combination of a receiver, transmitter, transceiver, speaker, keyboard, keypad, mouse, position tracked stylus, position tracked probe, foot switch, microphone, display, imaging sensor, or other input/output device or component of the PIU 100. The input/output interface 104 can be configured as an RS232 serial interface.

The communication interface 105 may be configured as a circuit, RS232 serial interface, or other device for communicating with elements or components included in the PIU 100, and external to the PIU 100 via a network. For example, the communication interface 105 may store information to be output in a transfer packet and output the transfer packet to an external apparatus via the network by communication technology such as Transmission Control Protocol/Internet Protocol (TCP/IP). The PIU 100 may include a plurality of communication circuits according to a desired communication form.

The display 106 can present a display to a user to view images, data or other information, and may be configured as one or more or a combination of a monitor, LCD, LED display, organic LED (OLED) display, plasma display, organic electro luminescence panel, or other type of display configuration. The PIU 100 can generate one or more of a graphical user interface (GUI) that is output to the display 106. The display 106 can be separate from or integrated in the PIU 100. The display 106 can display or output on the GUI or other screen one or more or a combination of an impact profile, event log, images being captured, captured images, captured moving images, icons, menus, digital boxes, instructions, data, information, or other types of information based on user input or other instructions. A user can select and activate GUI output by pointing and clicking with an input or pointing device, such as a mouse, keyboard, or the like.

The power source 107 provides power to the PIU 100 and includes one or more or a combination of internal and external power and can operate in one or more of a power-up mode, power-off mode, low power mode, sleep mode, or other modes or combinations thereof. The power source 107 provides power to the PIU 100 and can have battery backup to ensure the PIU 100 is always powered. In the power-up mode or the power-off mode or other modes, the PIU 100 is configured to detect and record sensor data regarding an impact event. Detection of an impact event occurs when the sensor 103 in the PIU 100 detect operational parameters that are equal to or exceed predetermined thresholds.

The power source 107 can include a battery contained in the PIU 100 and can include an external power source such as line power, alternating current (AC) power or direct current (DC) power from a power outlet that can interconnect with the PIU 100 through an AC/DC adapter and a DC/DC converter, or an AC/DC converter in order to adapt the power voltage from a source into one or more voltages used by components in the PIU 100. The power source 107 can include a rechargeable battery or battery cell and can receive external line power in the power-up or full power mode. The battery can supply power to each functional element of the PIU 100 can operate to have intermittent power during sensor operation and can operate to shut down components of the PIU 100 during non-use cycles. The battery can interconnect with an external power source to recharge the battery. The processor 101 can be taken offline when processing is complete to reduce power or current drain.

The components of the PIU 100 can receive power from the power source 107 in the power-up or full power mode, whereby the rechargeable battery can be recharged. The PIU 100 can include an integrated power switch that can be switched on or off in response to various sensor readings or other conditions. For example, in a case where impact has occurred, the battery can be switched from low power to power-on or full power mode to fully power the PIU 100. In the power-off or power conservation mode, components of the PIU 100 can be powered by the rechargeable battery in order to monitor and maintain impact events and conditions of the PIU 100 during normal procedure, transportation, and maintenance, and can receive reduced, minimal, or no power from the power source 107 to conserve power.

The bus 108 communicatively connects the components of the PIU boo to input devices, output devices, communication devices, or other devices. The bus 108 can be a system management bus (SMBus) to allow the power source 107 or battery to communicate with other components of the PIU 100. The input devices are configured to enable the user to communicate information and select commands to the PIU 100, and can include mouse(s), keyboards, touchscreens, or the like, with keys or buttons with alphanumeric or cursor controlled icons. The output devices are configured to display data or images generated by the PIU 100, and can include printers and display devices including, for example, an LCD, CRT, LED, OLED, or the like. The bus 108 can transmit and receive data between these pieces of hardware connected together, or transmit a command from the processor 101 to the other pieces of hardware.

The PIU 100 can include a battery charger that can connect to the battery, whereby the battery can be monitored during PIU operation while charging and discharging to determine the battery power status, battery charging rate, battery discharge rate, time remaining until discharge, or other types of information. The battery can be monitored at periodic or regular intervals or at random and variable indeterminate times. The battery charger can monitor the voltage state of the battery and determine whether the voltage of the battery is lower than or equal to a predetermined voltage, whether the voltage of the battery exceeds the predetermined voltage, whether the voltage of the battery is within a predetermined voltage range, or whether the voltage of the battery corresponds to another condition.

The power mode of the PIU 100 can automatically change depending on the battery information. The battery information can be communicated to a network that would allow for the flow of information between the battery, the processor, and other computers, servers, or devices that are connected to the network. The PIU 100 can include one or more LEDs or similar devices to provide a visual indication of impact status of the PIU 100, the battery information and the presence of any faults that would affect the operation of the battery or the PIU 100. The LEDs can indicate the health and capabilities of the battery or the PIU 100.

In the power-off mode, the battery or battery cells of the power source 107 can power up the sensor 103 and other components. If no impact occurs, the sensor 103 can go into a low power mode or to a sleep mode to preserve life of the battery or power source 107. If impact occurs, an interrupt is generated to wake up the sensor 103 and an impact profile can be generated or logged where information or data associated with the impact can be recorded or stored as the impact profile in the memory 102.

In the power-up mode, the PIU 100 or the host can interrogate the memory 102 and retrieve impact or other profile data regarding impacts or other events that are or currently taking place or have occurred to the PIU 100 at any particular time or that may have occurred during a particular or desired time range or time period that can be current, recent or in the past. The sensor 103 can read and transmit impact or other profile data from the memory 103 to the PIU 100 or externally to the host or other location. The PIU 100 can analyze the impact or other profile data based on one or more or a combination of an algorithm, calculation, or other process to determine whether any particular areas of the impact profile data have reached or exceeded certain predetermined impact levels to characterize the data in a desired manner, for example, as major, minor, critical or other types of characterization. The characterization type can correspond to various types of sensor readings including, for example, signal amplitude, pulse width, or other designations. The processor 101 of the PIU 100 is programmed or configured to distinguish between major and minor impact events where a minor or major impact event is identified based on a comparison between detected sensor readings or parameters and one or more threshold values. The processor 101 can execute software, computer code or instructions to analyze the sensor readings in real time or at a later time to determine operational parameters of the PIU 100.

In exemplary embodiments, the sensor 103 can monitor and respond to one or more or a combination of an impact force, impact position, impact parameter, drop, fall, or other characteristics or parameters of the PIU 100. The accelerometer sensor, for example, can monitor or measure the displacement of the PIU 100 with a position or sense the speed of a motion of the PIU 100. The gyroscope sensor can monitor or sense angular velocity or an angle of motion and can measure movement of the PIU 103 in up to six total degrees of freedom in three-dimensional space including three degrees of translation freedom along cartesian x, y, and z coordinates and orientation changes between those axes through rotation along one or more or of a yaw axis, a pitch axis, a roll axis, and a horizontal axis. Yaw is when the PIU 103 twists left or right on a vertical axis. Pitch is when the PIU 100 rotates from side to side. Roll is when the PIU 100 rotates on the front-to-back axis.

The sensor 103 can monitor and respond to power capacity of the power source or battery of the PIU 100. The sensor 103 can monitor shock or drop impact parameters with low power consumption, dynamic range, and bandwidth to accurately detect and capture shock events and convert them to a digital signal for processing. The sensor 103 can be a smart sensor that can process data in real time in connection with the processor 101 of the PIU 100. An impact profile, shock profile, collision profile, or other type of profile can be generated or developed based on sensor data, and can be characterized by peak amplitude and pulse width of the sensor data for further analysis. The sensor 103 and/or the processor 101 of the PIU 100 can interrogate the power status or capacity of the power source 107, and can warn a user to replace the battery at a time when a value of the battery capacity falls below a predetermined threshold amount.

The processor 101, for example, can store or log sensor data or information in the memory 102 or storage based on readings, signals, or measurements obtained by or recorded from the sensor 103. The processor 101 or a remote host can interrogate, query, or probe the sensor 103 to request, obtain, or record status readings or measurements from the sensor 103. Interrogations or data requests based on data or readings in the sensor 103 can take place at regular or irregular times. For example, the PIU 100 or a remote host can make independent interrogations of the sensor 103 at periodic or predetermined intervals. Interrogations of the sensor 103 can also be made at random, intermittent, or irregular times through user operation or in response to occurrence of one or more or a combination of normal, inadvertent, unexpected, or improper activity or event, or any other type of activity or event, such as an impact, fall, drop or other measured parameter, whereby the sensor readings or operational or parametric status of the sensor 103 can be determined and recorded. Current sensor readings, measurements, sensor logs, or event logs can be compared with previous readings, measurements, or sensor logs, or event logs of the sensor 103. The current and historical operational status of the sensor 103 can be determined and analyzed through the interrogations. Useful feedback can be developed and provided to users of the PIU 100 so appropriate action can take place including one or more or a combination of warnings, alerts, predictive maintenance scheduling, or other types of action. The sensor readings can be based on detected impacts, collisions, drops, falls, pressures, forces, vibrations, or other types of readings.

The monitored, detected, or recorded sensor readings, information, data, measurements, parameters, or other readings of the sensor 103 can be characterized based on various types of thresholds, ranges, or the like. Readings having values that fall within predetermined ranges can be characterized as normal or routine values or readings, and readings having values that fall outside the predetermined ranges can be characterized as major, minor, critical or other types of readings. In a case where impact, force, collision, or similar parameter values are detected, recorded, or analyzed, the readings can be considered normal or routine when they fall within a predetermined threshold range. The readings can be considered to be minor when the readings fall within a certain range outside the predetermined range. The readings can be considered to be major or critical when the readings fall outside the predetermined range beyond the certain range. A sensor reading that has a value below a predetermined threshold value or equals or is within the predetermined range can be considered normal or routine and can otherwise be disregarded. A sensor reading that has a value that exceeds the predetermined threshold value but is within a second threshold value can be considered as a minor reading. A sensor reading that has a value that exceeds the predetermined threshold value and the second threshold value or is outside the predetermined range can be considered as a major or critical reading. Readings that are outside the predetermined range can be accumulated and recorded as a log where an impact profile or event can be generated for each occurrence that is outside the predetermined range. Processing can determine whether the readings exceed the predetermined threshold value, the second threshold value or are outside of the predetermined range.

As the sensor 103 monitors, detects, or measures physical, operational, or parametric data of the PIU 100 over time, the information or data generated based on the detected data of the PIU 100 can be stored in memory or storage on the PIU 100 or remotely from the PIU 100. The information or data can also be transmitted wirelessly or through a hardwired connection over a network to a remote network location or host, data storage, cloud storage, or the like. The information can also be stored on one or more removable storage devices, such optical disks, memory cards, USB flash drives, DVDs, CDs, memory sticks, external hard drives, or the like.

For example, in a case where impact occurs, the impact can be detected or measured by the sensor 103, an impact profile can be generated based on the detected physical, operational or parametric data of the PIU 100 in multiple axes, and can be stored in memory or storage on the PIU 100 or remotely from the PIU 100. Impact, collision, shock, or other events of the PIU 100 can be monitored in multiple axes, in a multi-dimensional manner, or along an x axis, a y axis, a z axis, or any combination thereof.

During a collision or impact, the sensor 103 moves and can detect an acceleration change and rotation around a gravity axis, and the sensor 103 can output the information about the detected change and rotation. The processor 101 can acquire information about the change and rotation output from the sensor 103. In response to movement of the PIU 100, the sensor 103 obtains positional information about a place where the PIU 100 is located. The sensor can output the positional information as a sensor reading or information.

Impact profiles can be compared to implement threshold conditions that cause actionable activities that can include triggers that cause functional steps to be determined and analyzed in a measured manner, and can be transmitted to a host or remote server location to implement behavior of the PIU 100 based on whether sensor readings exceed predetermined levels so as to interrupt behavior. The processor 101 can check memory 102 and control components that behave improperly. Data processing can be performed to cause the steps to take place based on levels or measurements of the PIU 100 that can be compared with data that implements functional activity that implements the memory 102 to interrupt activity based on whether the impact causes a triggering event based on detection of impact at a value or level above a predetermined threshold. The impact can be due to the PIU 100 being dropped, mishandled, shaken, tossed, rotated, thrown, or other types of physical movement or disturbance.

Triggering events can include one or more or a combination of detection of impact, drop, fall, temperature, pressure, voltage, current, strain, timing, power, user activity, moisture, shipping, tampering, mishandling, battery failure, battery replacement, or other types of events, or combinations thereof.

Figure 4:
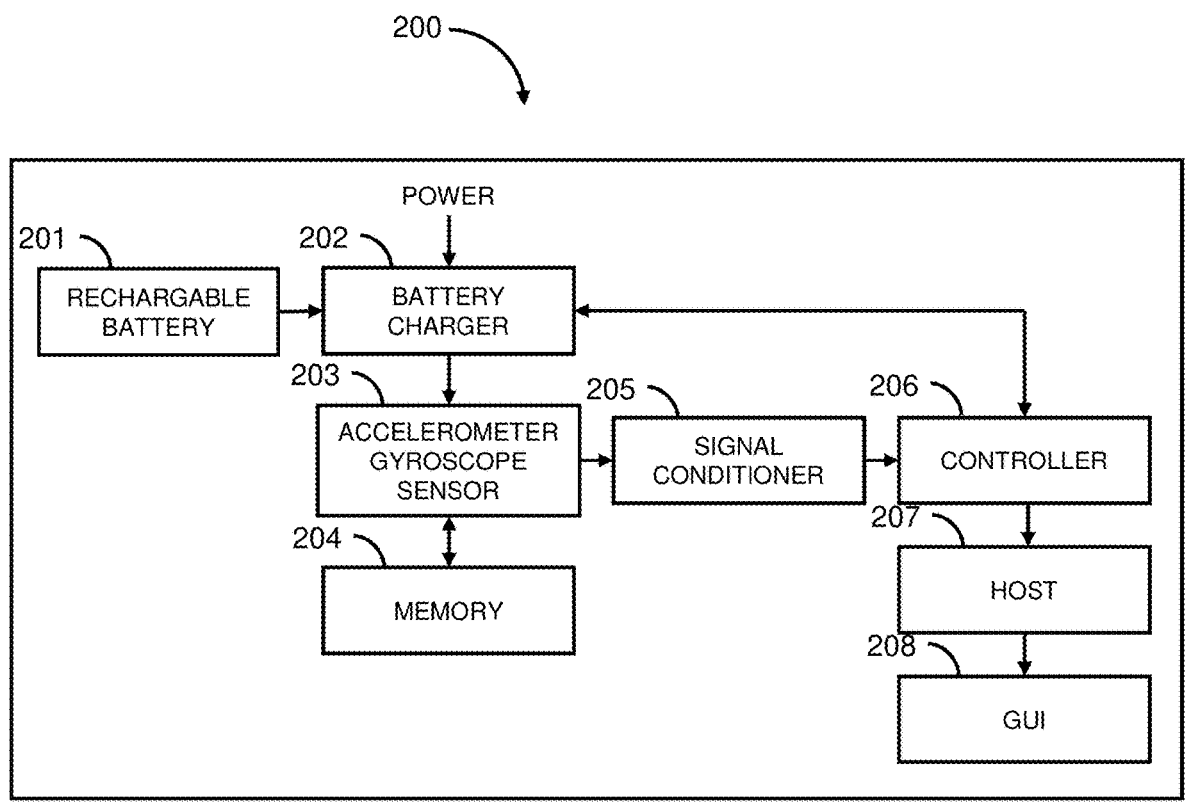
FIG. 4 is a block diagram illustrating an example of a hardware configuration of a PIU 200 according to one or more embodiments.

The PIU 100 of FIGS. 2 and 3 may be implemented in the present embodiment. FIG. 4 is a PIU drop detection block diagram showing a PIU 200 as an exemplary medical apparatus according to some embodiments.

Figure 5:
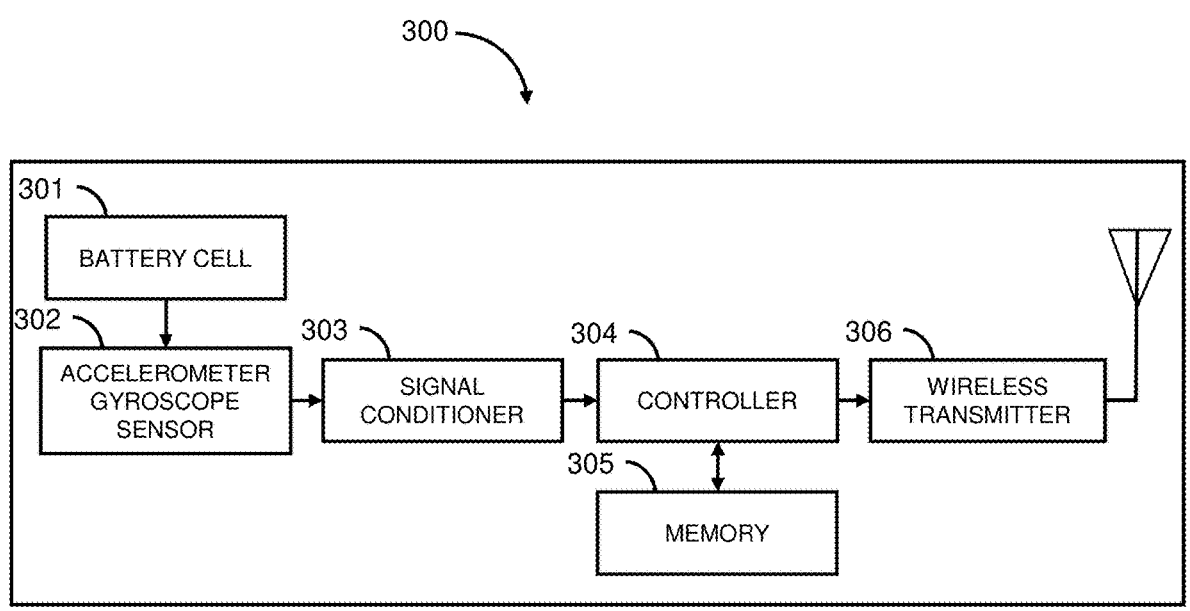
FIG. 5 is a block diagram illustrating an example of a hardware configuration of a PIU 300 according to one or more embodiments.

FIG. 5 illustrates a PIU 30o as an exemplary medical apparatus according to some embodiments.

The PIU 200 is configured to measure, detect, sense, record, or otherwise monitor impacts, drops, falls, or other conditions of the PIU 200, and has one or more or a combination of a rechargeable battery 201, a battery charger 202, an accelerometer gyroscope sensor 203, a memory 204, a signal conditioner 205, a controller 206, a host 207, and a GUI 208, and can include other elements or components.

The PIU 200 can include a physical and impact drop detection sensor, located in a PIU assembly, see FIG. 1. The impact sensor can be a combination of acceleration and gyroscope sensors. Accelerometer sensors measure the displacement of a mass with a position, and gyroscopes, however, measure angular velocity. The 3-axis accelerometer/gyroscope sensor can monitor shocks along any combination of x, y, and/or z axes with low power consumption, dynamic range, and bandwidth to accurately detect and capture the shock events. The conditioned sensor's output is converted to it to a digital signal for post processing.

The accelerometer/gyroscope sensor 203 and the memory 204 are powered by a rechargeable battery 201 or battery cell when an MMOCT system is powered down in order to monitor and maintain the impact events during normal procedure, transportation, and maintenance.

Built-in gyroscopes and accelerometers are able to calculate the motion and rotation of the device and move the sensor accordingly to keep the image stable. The gyroscopes can provide stabilization along five axes: yaw, pitch, roll, horizontal and vertical. Yaw is when the device twists left or right on a vertical axis. Rotation on the front-to-back maxi is called roll. Rotation from side to side is called pitch.

Once an impact is detected, the impact profile can be transferred to a memory for storage. The memory 204 can be an external non-volatile memory EEPROM. Sub-sequentially next impacts events detection can be stored in the memory.

The sensor output can be fed to a signal conditioner 205 to remove any unwanted noise, demodulation, low pass filtering before it gets to the controller 206.

During MMOCT system power up, the stored impact profiles can be available to the PIU controller 206 for interrogation. The PIU controller 206 can request the impact profiles after system initialization, and determines based on the impact algorithm detection if the impact is a minor impact or a major impact.

Upon request from a host, the PIU controller 206 can transfer log event profiles to the host, via RS232 serial interface or other communication and can warn the user via a console GUI and via LED indicator(s) located in the PIU 200, if the PIU 200 is damaged.

The PIU controller 206 can also interrogate the battery 201 capacity status, via a SMbus serial interface communication, and can warn the user if it is time to replace the battery cell.

FIG. 5 illustrates a PIU 30o as an exemplary medical apparatus according to some embodiments.

The PIU 30o is configured to measure, detect, sense, record, or otherwise monitor impacts, drops, falls, or other conditions of the PIU 300, and has one or more or a combination of a battery cell 301, an accelerometer/gyroscope sensor 302, a signal conditioner 303, a controller 304, a memory 305, and a wireless transmitter 306, and can include other elements or components.

The PIU 300 can include a physical and impact drop detection sensor, located in the PIU 300. The impact sensor can be a combination of acceleration and gyroscope sensors. Accelerometer sensors measure the displacement of a mass with a position, and gyroscopes, however, measure angular velocity. The 3-axis accelerometer/gyroscope sensor can monitor shocks along any combination of x, y, and/or z axes with low power consumption, dynamic range, and bandwidth to accurately detect and capture the shock events. The conditioned sensor's output is converted it to a digital signal for post processing.

The accelerometer/gyroscope sensor 302 and the memory 305 are powered by the battery cell 301 when an MMOCT system is powered down in order to monitor and maintain the impact events during normal procedure, transportation, and maintenance.

Built-in gyroscopes and accelerometers are able to calculate the motion and rotation of the device and move the sensor accordingly to keep the image stable. The gyroscopes can provide stabilization along five axes: yaw, pitch, roll, horizontal and vertical. Yaw is when the device twists left or right on a vertical axis. Rotation on the front-to-back maxi is called roll. Rotation from side to side is called pitch.

Once an impact is detected, the impact profile can be transferred to a memory for storage. The memory 305 can be an external non-volatile memory EEPROM. Sub-sequentially next impacts events detection can be stored in the memory.

The sensor output can be fed to a signal conditioner 303 to remove any unwanted noise, demodulation, low pass filtering before it gets to the controller 304.

During MMOCT system power up, the stored impact profiles can be available to the PIU controller 304 for interrogation. The PIU controller 304 can request the impact profiles after system initialization, and determines based on the impact algorithm detection if the impact is a minor impact or a major impact.

In this embodiment, the sensor interrogation is the same as the previous embodiment. The PIU controller 304 converts the impact sensor into a smart impact sensor.

The impact profile data transmission to the host can be done wirelessly, instead of serially via RS232 interface.

The PIU 300 includes standalone circuitry that continuously monitors the sensor output and can feed the conditioned sensor's signal to the controller 304, can store event profiles in non-volatility external memory, and can transmit the event wirelessly to the host. In this configuration, a PIU cable can be bypassed in case of a damaged cable.

The following describes a system power-off mode and a power-on mode of operation that can be used for some embodiments.

System Power-Off Mode:

Battery cell powers up the impact sensor and the non-volatile memory circuitries.

If no impact occurs, the sensor will go into a low power mode or to a sleep mode to preserve battery cell life power.

If impact occurs, an interrupt is generated, hence waking up the impact sensor and login any event information into external memory. Then goes into sleep mode until next impact events occurs.

System Power-Up Mode:

After power up initialization, the PIU controller can interrogate the impact sensor profile data.

The impact sensor can read and transmit event or impact profiles from an external non-volatile memory to the PIU controller, or directly to the host.

The PIU controller can determine based on the impact profile algorithm detection if the impact is critical or not. An algorithm can be based on the characterization of signal peak amplitude and pulse width.

Features of the present disclosure include the following.

PIU drop detection profile characterization during misuse of the PIU subsystem in the field and during shipment.

Identify a potential failure due to the drop test.

Display via GUI warnings of potential failure.

Distinguish between a minor impact and a major impact.

Increase MMOCT reliability.

Wirelessly transmit log event files.

Rechargeable battery cell.

Log PIU impact event profiles.

Continuously monitor rotational and acceleration PIU impacts.

Externally impact data storage in non-volatile memory.

Transfer PIU impact log files to the HOST, via serial communication interface.

Configuration

Main System (cart, medical system)

Remote opto-mechanical unit (PIU, wired or non-wired)

Accelerometer (drop sensor)

Microcontroller

Memory

Rechargeable battery cell

Wireless transmitter.

Accelerometer (drop sensor) continuously monitoring rotation and acceleration PIU experiences.

Microcontroller

Detects PIU acceleration

Characterizes the acceleration profile (during misuse of the PIU subsystem in the field and during shipment).

Distinguishes between a minor impact and a major impact.

Identifies a potential failure due to the drop.

Stores impact data in non-volatility memory storage.

Log PIU impact event profiles.

Wirelessly transmitted log event files.

Wireless transmitter transfers PIU impact log files to the host, via serial communication interface.

Main system displays via GIU warnings of potential failure.

Functions

The drop sensor system goes in sleep (low power mode) when the system is not powered.

The drop sensor system is powered by the battery cell.

The drop sensor system wakes up when it detects impact.

As described above, a medical apparatus, method and storage medium according to one or more aspects of the present disclosure can monitor a sensor of the medical apparatus to obtain a sensor reading, perform impact detection based on the sensor reading, generate an impact profile based on the impact detection, characterize the impact detection, and respond to the impact detection.

The medical apparatus, method and storage medium can also detect damage of the medical apparatus based on the sensor reading, visually indicate impact status of the medical apparatus with one or more LEDs, predict field service maintenance of the medical apparatus based on the sensor reading, and can perform other operations or functions.

The sensor reading can be a plurality of sensor readings, and the sensor can include one or more of an acceleration sensor, a gyroscope sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, and a depth sensor.

The medical apparatus, method and storage medium can also generate an impact log and log the impact profile in the impact log, characterize the impact detection as major, minor, normal, or critical based on one or more sensor readings having a value within or outside of a predetermined range, trigger an event based on the impact detection, generating a warning based on the impact detection.

The medical apparatus, method and storage medium can also power the medical apparatus with a power source, interrogate power status of the power source, switch power modes based on activity of the medical apparatus, the power modes including one or more or a combination of a power-on mode, a power-off mode, a sleep mode, and a low power mode.

The power source can be a rechargeable battery and the medical apparatus, method and storage medium can also charge the battery with a battery charger, interrogate power status of the battery, provide visual indication of the power status of the battery with one or more light emitting diodes (LEDs), transmit the power status of the battery to one or more computing configurations through a network, and can perform other functions or operations.

The medical apparatus, method or storage medium can also provide the medical apparatus with a display with a GUI, wherein the GUI can allow interaction with the medical apparatus through graphics, audio, or combinations thereof.

The medical apparatus, method or storage medium can also perform wired or wireless communication with the medical apparatus through a network, remotely interrogate the at least one sensor by one or more computing configurations through a network, and can perform sensor reading processing using artificial intelligence or machine learning.

Additional features or aspects of present disclosure can also advantageously implement one or more AI (artificial intelligence) or machine learning algorithms, processes, techniques, or the like, to monitor a sensor of the medical apparatus to obtain a sensor reading, perform impact detection based on the sensor reading, generate an impact profile based on the impact detection, characterize the impact detection, and respond to the impact detection as described above or otherwise contribute to facilitate precision impact profile generation and impact detection. Such AI techniques use a neural network, a random forest algorithm, a cognitive computing system, a rules-based engine, or the like, and are trained based on a set of data to assess types of data and generate output. For example, a training algorithm can be configured to facilitate monitoring a sensor of the medical apparatus to obtain a sensor reading, performing impact detection based on the sensor reading, generating an impact profile based on the impact detection, characterizing the impact detection, and responding to the impact detection. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the sensor monitoring of the medical apparatus to obtain a sensor reading, impact detection based on the sensor reading, generating an impact profile based on the impact detection, characterization of the impact detection, and response to the impact detection can be used as input data and provided to the training algorithm. Sensor readings can be stored in a database to facilitate impact profile and impact detection that are generated using input mapping to the model(s) or through expert research, and machine learning can find parameters for AI processes. Impact profile and impact detection data from the initial data sets are used or placed into an AI process or algorithm to facilitate impact profile and impact detection for new data. The training algorithm is configured to learn physical relationships in the input data to best describe these relationships or correlations. The data sets include information based on a number of factors including, for example, the acquired sensor readings, characterization of the impact detection, and response to the impact detection, or the like. The data is evaluated using a weighted evaluation where the weights are learned through a training process, through subject matter specifications, or the like. Deep learning mechanisms can augment an AI process to identify indicators in the sensor readings that can include, for example, the acquired sensor readings, characterization of the impact detection, and response to the impact detection, or the like.

The algorithm(s) described herein is a set of computer executable instructions that are executed by a medical apparatus. The apparatus can be interconnected with medical instruments or a variety of other devices, and may be controlled independently, externally, or remotely through components including, for example, one or more processors, one or more I/O components, and storage. The one or more processors include one or more central processing units (CPUs), which may include one or more microprocessors (e.g., a single core microprocessor, a multi-core microprocessor); one or more graphics processing units (GPUs); one or more tensor processing units (TPUs); one or more application-specific integrated circuits (ASICs); one or more field-programmable-gate arrays (FPGAs); one or more digital signal processors (DSPs); or other electronic circuitry (e.g., other integrated circuits). The I/O components include communication components (e.g., a graphics card, a network-interface controller) that communicate with a display device and a network, and other input or output devices (not illustrated), which may include a keyboard, a mouse, a printing device, a touch screen, a light pen, an optical-storage device, a scanner, a microphone, a drive, and a game controller (e.g., a joystick, a gamepad).

OTHER EMBODIMENTS

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., ASIC) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., CPU, MPU, or the like), and may include a network of separate computers or separate processors to read out and execute the computer executable instructions. The computer executable instructions may be provided to the computerized configuration(s), for example, from a network or the storage medium. The storage medium may include, for example, one or more of a hard-disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An MMOCT (multi-modality optical coherence tomography) apparatus with a PIU (patient interface unit) comprising:
    at least one sensor;
    at least one memory; and
    at least one processor which performs:
    monitoring a sensor to obtain a sensor reading;
    performing impact detection based on the sensor reading;
    generating an impact profile based on the impact detection;
    storing the impact profile in a memory;
    characterizing the impact detection based on one or more sensor readings having a value within or outside of a predetermined range;
    triggering an event to implement behavior of the PIU when the impact detection is at a level above a predetermined threshold;
    communicatively interconnecting the PIU with a host through a network;
    remotely interrogating the sensor and power status of the PIU to obtain operational parameters of the PIU;
    determining and analyzing current and historical operational status of the PIU based on the impact profile and interrogation of the sensor and power status of the PIU;
    wirelessly transmitting the operational parameters and operational status of the PIU through the network; and
    responding to the impact detection by changing behavior of the PIU when the impact detection is at a level above the predetermined threshold.

2. The MMOCT apparatus according to claim 1, wherein the at least one processor further performs detecting damage of the medical apparatus based on the sensor reading.

3. The MMOCT apparatus according to claim 1, wherein the at least one processor further performs visually indicating impact status of the medical apparatus with one or more light emitting diodes (LEDs) based on the sensor reading.

4. The MMOCT apparatus according to claim 1, wherein the at least one processor further performs predicting field service maintenance of the medical apparatus based on the sensor reading.

5. The MMOCT apparatus according to claim 1, wherein the sensor reading is a plurality of sensor readings.

6. The MMOCT apparatus according to claim 1, wherein the at least one sensor comprises one or more of an acceleration sensor, a gyroscope sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, and a depth sensor.

7. The MMOCT apparatus according to claim 1, wherein the at least one processor further performs generating an impact log and logging the impact profile in the impact log.

8. The MMOCT apparatus according to claim 1, wherein the at least one processor further performs characterizing the impact detection as major, minor, normal, or critical.

9. The MMOCT apparatus according to claim 1, wherein the at least one processor further performs generating a warning based on the impact detection.

10. The MMOCT apparatus according to claim 1, further comprising a power source to power the medical apparatus.

11. The MMOCT apparatus according to claim 10, wherein the at least one processor further performs switching power modes based on activity of the MMOCT apparatus, the power modes including one or more or a combination of a power-on mode, a power-off mode, a sleep mode, and a low power mode.

12. The MMOCT apparatus according to claim 10, wherein the power source is a rechargeable battery.

13. The MMOCT apparatus according to claim 12, further comprising a battery charger to charge the rechargeable battery.

14. The MMOCT apparatus according to claim 12, wherein the at least one processor further performs interrogating power status of the battery.

15. The MMOCT apparatus according to claim 14, further comprising one or more light emitting diodes (LEDs) to provide visual indication of the power status of the battery.

16. The MMOCT apparatus according to claim 14, wherein the at least one processor further performs transmitting the power status of the battery to one or more computing configurations through the network.

17. The MMOCT apparatus according to claim 1, further comprising a display with a graphical user interface (GUI).

18. The MMOCT apparatus according to claim 17, wherein the GUI is configured to allow interaction with the MMOCT apparatus through graphics, audio, or combinations thereof.

19. The MMOCT apparatus according to claim 1, wherein the at least one processor further performs wired or wireless communication through the network.

20. The MMOCT apparatus according to claim 1, wherein the at least one processor further performs sensor reading processing using artificial intelligence or machine learning.

21. A method for an MMOCT (multi-modality optical coherence tomography) apparatus with a PIU (patient interface unit) and at least one sensor, the method comprising:
monitoring a sensor of the MMOCT apparatus to obtain a sensor reading;
performing impact detection based on the sensor reading;
generating an impact profile based on the impact detection;
storing the impact profile in a memory;
characterizing the impact detection based on one or more sensor readings having a value within or outside of a predetermined range;
triggering an event to implement behavior of the PIU when the impact detection is at a level above a predetermined threshold;
communicatively interconnecting the PIU with a host through a network;
remotely interrogating the sensor and power status of the MMOCT apparatus to obtain operational parameters of the MMOCT apparatus;
determining and analyzing current and historical operational status of the PIU based on the impact profile and interrogation of the sensor and power status of the PIU;
wirelessly transmitting the operational parameters and operational status of the PIU through the network; and
responding to the impact detection by changing behavior of the PIU when the impact detection is at a level above the predetermined threshold,
wherein the communicatively interconnects with a host through the network.

22. The method according to claim 21, further comprising detecting damage of the MMOCT apparatus based on the sensor reading.

23. The method according to claim 21, further comprising visually indicating impact status of the MMOCT apparatus with one or more light emitting diodes (LEDs) based on the sensor reading.

24. The method according to claim 21, further comprising predicting field service maintenance of the MMOCT apparatus based on the sensor reading.

25. The method according to claim 21, wherein the sensor reading is a plurality of sensor readings.

26. The method according to claim 21, wherein the at least one sensor comprises one or more of an acceleration sensor, a gyroscope sensor, a proximity sensor, a motion sensor, a position sensor, a rotation sensor, a magnetic sensor, a barometric sensor, an illumination sensor, a pressure sensor, an angular position sensor, a temperature sensor, an altimeter sensor, an infrared sensor, a sound sensor, an air monitoring sensor, a piezoelectric sensor, a strain gauge sensor, a sound sensor, a vibration sensor, and a depth sensor.

27. The method according to claim 21, further comprising generating an impact log and logging the impact profile in the impact log.

28. The method according to claim 21, further comprising characterizing the impact detection as major, minor, normal, or critical.

29. The method according to claim 21, further comprising generating a warning based on the impact detection.

30. The method according to claim 21, further comprising powering the medical apparatus with a power source.

31. The method according to claim 30, further comprising switching power modes based on activity of the MMOCT apparatus, the power modes including one or more or a combination of a power-on mode, a power-off mode, a sleep mode, and a low power mode.

32. The method according to claim 30, wherein the power source is a rechargeable battery.

33. The method according to claim 32, further comprising charging the battery with a battery charger.

34. The method according to claim 32, further comprising interrogating power status of the battery.

35. The method according to claim 34, further comprising providing visual indication of the power status of the battery with one or more light emitting diodes (LEDs).

36. The method according to claim 34, further comprising transmitting the power status of the battery to one or more computing configurations through the network.

37. The method according to claim 21, further comprising providing the MMOCT apparatus with a display with a graphical user interface (GUI).

38. The method according to claim 21, wherein the GUI is configured to allow interaction with the MMOCT apparatus through graphics, audio, or combinations thereof.

39. The method according to claim 21, further comprising performing wired or wireless communication with the MMOCT apparatus through the network.

40. The method according to claim 21, further comprising performing sensor reading processing using artificial intelligence or machine learning.

41. A non-transitory computer readable storage medium storing a program for causing a computer to execute a method for an MMOCT (multi-modality optical coherence tomography) apparatus with a PIU (patient interface unit) and at least one sensor, the method comprising:
- monitoring a sensor of a medical apparatus to obtain a sensor reading;
- performing impact detection based on the sensor reading;
- generating an impact profile based on the impact detection;
- storing the impact profile in a memory;
- characterizing the impact detection based on one or more sensor readings having a value within or outside of a predetermined range;
- triggering an event to implement behavior of the PIU when the impact detection is at a level above a predetermined threshold;
- communicatively interconnecting the PIU with a host through a network;
- remotely interrogating the sensor and power status to obtain operational parameters of the MMOCT apparatus;
- determining and analyzing current and historical operational status of the PIU based on the impact profile and interrogation of the sensor and power status of the PIU;
- wirelessly transmitting the operational parameters and operational status of the PIU through the network; and
- responding to the impact detection by changing behavior of the PIU when the impact detection is at a level above the predetermined threshold.

* * * * *